United States Patent
Dobel et al.

(10) Patent No.: US 10,370,155 B2
(45) Date of Patent: Aug. 6, 2019

(54) MATERIAL AND PACKAGING FOR YEAST STORAGE

(71) Applicant: LESAFFRE ET COMPAGNIE, Paris (FR)

(72) Inventors: Sandrine Dobel, Cysoing (FR); Anthony Bernard Malaquin, Provin (FR)

(73) Assignee: LESAFFRE ET COMPAGNIE, Paris (FR)

( * ) Notice: Subject to any disclaimer, the term of this patent is extended or adjusted under 35 U.S.C. 154(b) by 367 days.

(21) Appl. No.: 14/363,838

(22) PCT Filed: Dec. 13, 2012

(86) PCT No.: PCT/FR2012/052914
§ 371 (c)(1),
(2) Date: Jun. 9, 2014

(87) PCT Pub. No.: WO2013/088074
PCT Pub. Date: Jun. 20, 2013

(65) Prior Publication Data
US 2014/0367299 A1 Dec. 18, 2014

(30) Foreign Application Priority Data
Dec. 14, 2011 (FR) ..................... 11 61599

(51) Int. Cl.
| | | |
|---|---|---|
| *B32B 1/02* | (2006.01) | |
| *B65D 33/01* | (2006.01) | |
| *B32B 27/30* | (2006.01) | |
| *C12N 1/04* | (2006.01) | |
| *C12N 1/18* | (2006.01) | |
| *B65D 85/72* | (2006.01) | |
| *B32B 7/02* | (2019.01) | |
| *B32B 27/08* | (2006.01) | |
| *B32B 27/34* | (2006.01) | |
| *B32B 27/36* | (2006.01) | |
| *B32B 3/26* | (2006.01) | |
| *B32B 1/08* | (2006.01) | |

(52) U.S. Cl.
CPC .............. *B65D 33/01* (2013.01); *B32B 3/266* (2013.01); *B32B 7/02* (2013.01); *B32B 27/08* (2013.01); *B32B 27/306* (2013.01); *B32B 27/34* (2013.01); *B32B 27/36* (2013.01); *B65D 85/72* (2013.01); *C12N 1/04* (2013.01); *C12N 1/18* (2013.01); *B32B 2250/24* (2013.01); *B32B 2250/40* (2013.01); *B32B 2270/00* (2013.01); *B32B 2307/724* (2013.01); *B32B 2307/7244* (2013.01); *B32B 2439/40* (2013.01); *B32B 2439/70* (2013.01)

(58) Field of Classification Search
CPC ......... B32B 1/02; B32B 27/36; B32B 27/306; B32B 7/02; B32B 3/266; B32B 2250/40; B32B 2270/00; B32B 2307/7244; B32B 2439/70; Y10T 428/1352; B65D 33/01; B65D 85/72; C12N 1/18
See application file for complete search history.

(56) References Cited

U.S. PATENT DOCUMENTS

| | | | | |
|---|---|---|---|---|
| 2,947,735 | A * | 8/1960 | Bartl | C08F 10/00 526/212 |
| 3,663,038 | A * | 5/1972 | Hendricks | B62K 9/02 188/5 |
| 4,863,770 | A | 9/1989 | Knox et al. | |
| 4,911,936 | A * | 3/1990 | Kijima | C12C 12/006 426/16 |
| 5,093,450 | A * | 3/1992 | Baade | C08F 210/02 526/323.2 |
| 5,427,943 | A * | 6/1995 | Suoranta | C12N 1/18 426/62 |
| 5,726,229 | A | 3/1998 | Bekele | |
| 6,153,232 | A * | 11/2000 | Holten | B65B 9/093 206/5 |
| 2005/0119364 | A1 * | 6/2005 | Grah | B29C 71/04 522/150 |
| 2006/0110512 | A1 * | 5/2006 | Blomme | B67D 1/1227 426/523 |
| 2007/0042089 | A1 * | 2/2007 | Grah | B29C 71/04 426/106 |

(Continued)

FOREIGN PATENT DOCUMENTS

| | | |
|---|---|---|
| DE | 3744214 | 7/1989 |
| DE | 3744214 A1 * | 7/1989 |
| EP | 0134142 A2 * | 3/1985 |
| EP | 1 059 163 | 12/2000 |
| EP | 2 019 051 | 1/2009 |
| WO | WO 2004/012939 | 2/2004 |
| WO | WO 2004/048253 | 6/2004 |

OTHER PUBLICATIONS

S. Mangaraj et al., Applications of Plastic Films for Modified Atmosphere Packaging of Fruits and Vegetables: A Review, Food Eng. Rev. (2009) vol. 1, p. 133-158.
S. Marais, et al., Study of Transport of Small Molecules Through Ethylene-Co-vinyl Acetate Copolymers Films. Part B: $CO_2$ and $O_2$ Gases, Polymer Testing (2002) vol. 21, p. 425-431.

*Primary Examiner* — Marc A Patterson
(74) *Attorney, Agent, or Firm* — Duane Morris LLP; Thomas J. Kowalski; Deborah L. Lu

(57) ABSTRACT

The invention relates to the use of a three-layer plastic film that is permeable to carbon dioxide but slightly impermeable to oxygen, as packing for liquid or semi-liquid products which produce gas. When the plastic film is reinforced with a uniformly perforated second plastic film, the resulting material is suitable for the manufacture of packaging for the storage of liquid or semi-liquid products containing yeasts, such as cream yeast.

12 Claims, No Drawings

(56) References Cited

U.S. PATENT DOCUMENTS

| | | | |
|---|---|---|---|
| 2007/0048410 A1* | 3/2007 | Rojas de Gante | ............................ B65D 81/3438 426/106 |
| 2009/0123399 A1* | 5/2009 | van Amerongen | ....... A23L 2/02 424/59 |
| 2009/0229287 A1* | 9/2009 | Prentner | ............... F25D 17/042 62/176.1 |
| 2011/0014320 A1* | 1/2011 | Zable | ...................... A23L 2/395 426/19 |

* cited by examiner

MATERIAL AND PACKAGING FOR YEAST STORAGE

CROSS REFERENCE TO RELATED APPLICATIONS

The present application is filed pursuant to 35 U.S.C. § 371 as a U.S. National Phase application of International Patent Application No. PCT/FR2012/052914, which was filed on Dec. 13, 2012, claiming the benefit of priority to French Patent Application No. FR 11 61599 filed on Dec. 14, 2011. The entire content of each of the aforementioned patent applications is incorporated herein by reference in its entirety.

FIELD OF THE INVENTION

The present invention relates to the field of packing and to the storage of liquid or semi-liquid products which produce gas, preferably carbon dioxide ($CO_2$), and concerns more particularly materials for packaging liquid or semi-liquid products containing yeasts or leavens.

BACKGROUND OF THE INVENTION

Yeast in aqueous suspension, when it is stored under favorable conditions, has indisputable advantages compared with yeasts in solid form, so-called pressed or dried yeast, in particular because of its simplified use, the fact that it is pre-dosed, and its good performance levels which, moreover, make it a product that is appreciated by those working in the bakery trade. As it happens, yeast in aqueous suspension is a product that is very sensitive to its storage conditions, in particular its environment (temperature, pH, $CO_2$/$O_2$ content, etc.), and particularly exposed to contaminations. It is thus a product difficult to package which thus requires hygienic storage conditions which at the same time make it possible to maintain its microbiological quality, its performance levels, in particular in terms of fermenting capacity, and its organoleptic qualities. In addition, the activity and the reactivity of a yeast, while they are responsible for good performance levels during its use, constitute a drawback specific to the storage of such a product. For good storage of the yeast, it is therefore desirable in practice to maintain said yeast in aqueous suspension at low temperature, of about 4° C., and to provide for specific degassing means, in particular for the release of the gases resulting from the yeast respiration metabolism, in particular carbon dioxide, while at the same time limiting the other gas exchanges (oxygen from the ambient air) in particular in order to avoid the development of contaminations.

Several solutions for packaging yeast in aqueous suspension have been proposed. One of these solutions consists in packaging the liquid yeast in a Bag-in-Box. The principle of the Bag-in-Box is to have, in a box generally made of cardboard (see, for example, American U.S. Pat. No. 6,223,981), a flexible bag which has one or more filling and/or emptying orifices, called bases (see, for example, American U.S. Pat. No. 4,863,770). Each base may have a screw thread or rings making it possible, respectively, to screw on or clip on a cap. The Bag-in-Box thus formed may be stored, for several weeks, at a temperature of between 0 and 6° C. and at a relative humidity of between 50% and 100%. The user may recover a given amount of yeast in aqueous suspension thus stored using a valve or a tap attached to a base after having removed the cap. In the case where a valve is put in place, the user turns the Bag-in-Box completely upside down and places it in an appropriate refrigerated dispenser (see, for example, the system described by the present applicant in international application WO 2004/048253). In the case where a tap is put in place, the Bag-in-Box is placed in the horizontal position in a refrigerator or a cold room.

In order to avoid swelling of the flexible bag contained in the carton of the Bag-in-Box under the action of the carbon dioxide produced by the yeast, orifices forming vents are provided for as specific degassing means (see, for example, European patent EP 0 792 930-B1 and international application WO 2004/048253 from the Applicant). Furthermore, the flexible bag is proportioned so as to leave a sufficient headspace in the Bag-in-Box to allow the gas to be stored until a sufficient pressure allowing evacuation of the gas through the degasser cap is reached. However, this degassing system is not entirely satisfactory, in particular when the liquid yeast stored is a non-stabilized yeast which produces larger amounts of $CO_2$ than stabilized yeast. Indeed, the swelling of the flexible bag, which may cause a deformation of the carton, giving it a bulging appearance, creates not only problems of stability of the Bag-in-Box, but may also prevent its insertion into the refrigerated dispenser. In certain cases, the swelling can lead to rupture of the carton. Furthermore, if the Bag-in-Box is under pressure, the opening thereof by the user may produce a geyser of product. Finally, when a Bag-in-Box is transported or handled, if the yeast comes into contact with the degasser cap, the latter may be momentarily or permanently clogged.

Application EP 2 019 051 by the present Applicant describes a packaging for a liquid product containing yeast comprising a permeable material which has an S/M ratio (exchange surface area S of the material expressed in $cm^2$ relative to the mass M of the liquid product containing yeast expressed in grams), and coefficients of oxygen ($O_2$) permeability and of carbon dioxide ($CO_2$) permeability determined so as, in particular, to avoid swelling of the product and to prevent the penetration of contaminants. However, such an S/M ratio does not allow much freedom regarding the choice of the shape and the dimensions of the pouch.

Therefore, there is a need for packagings which are suitable for the storage and maintaining of liquid products containing yeast and which allow better degassing of the $CO_2$ produced by yeast respiratory metabolism.

SUMMARY OF THE INVENTION

Generally, the present invention is based on the use of a multilayer plastic film having a B-A-B' structure with a specific composition, and thickness and gas-permeability properties that can be used to form the internal part of the flexible bag of a Bag-in-Box system. Contrary to the existing degassing systems, the degassing obtained through using a film of the present invention is constant over time and uniform over the entire surface of the bag. It therefore avoids the swelling of the flexible bag and all the potential problems associated with this swelling.

More specifically, in a first aspect, the present invention relates to a three-layer plastic film with a B-A-B' structure as wrapping/packing for a liquid or semi-liquid ingredient which produces gas, preferably carbon dioxide ($CO_2$), characterized in that:
  layer A consists of a polymer chosen from polymethylpentene (PMP) and olefinic copolymers, and
  each of layers B and B' comprises a polymer chosen from polymethylpentene (PMP) and olefinic copolymers, and characterized in that:
  the permeability of the film to carbon dioxide ($CO_2$), measured according to ISO standard 15105-2:2003 annex B, is greater than or equal to 80 $l/m^2 \cdot 24$ h at delta P=1 bar,
  the layers making up the film are extruded to a total thickness of from 20 to 50 microns, preferably from 25 to 35 microns, and
  the permeability of the film to oxygen ($O_2$), measured according to ISO standard 15105-2:2003 annex B, is less than or equal to 30 $l/m^2 \cdot 24$ h at delta P=1 bar.

In certain embodiments, the permeability of the film to carbon dioxide, measured according to ISO standard 15105-2:2003 annex B, is greater than or equal to 90 $l/m^2 \cdot 24$ h at delta P=1 bar.

In certain embodiments, the olefinic copolymers comprise, in particular, ethylene copolymers, in particular ethylene-vinyl acetate (EVA) and ethylene-polyvinyl alcohol (EVOH). In certain embodiments, the composition of layer B and the composition of layer B' are identical. In other embodiments, the composition of layer B and the composition of layer B' are different.

In certain particular embodiments of the invention, layer A consists of an ethylene-vinyl acetate (EVA) with a high vinyl acetate content, and each of layers B and B' comprises an ethylene-vinyl acetate (EVA) having a vinyl acetate content which is less than the vinyl acetate content of the ethylene-vinyl acetate of layer A. In certain embodiments, the vinyl acetate content of the EVA included in layer B is identical to the vinyl acetate content of the EVA included in layer B'. In other embodiments, these contents are different. In certain embodiments, the EVA with a high vinyl acetate content comprises, as percentage by weight, between 18% and 42% of vinyl acetate.

Each of layers B and B' may also comprise at least one anti-block and/or slip agent. In certain embodiments, layers B and B' comprise one or more identical anti-block and/or slip agents in the same proportions or in different proportions. In other embodiments, layers B and B' comprise one or more different anti-block and/or slip agents. In yet other embodiments, one of layers B and B' comprises one or more anti-block and/or slip agents and the other layer does not comprise more anti-block and/or slip agents.

In a second aspect, the present invention relates to a plastic material composed of two plastic films, characterized in that the first plastic film is a three-layer plastic film of the invention, and the second plastic film is uniformly perforated or has a permeability to $CO_2$ which is greater than or equal to that of the first plastic film.

In one particular embodiment of the invention, the second plastic film is composed of oriented polyamide (OPA) and polyethylene (PE) or of polyethylene terephthalate (PET) and polyethylene (PE).

In a third aspect, the present invention relates to a packaging comprising a reservoir/container composed of a plastic material of the invention, characterized in that the first plastic film of the plastic material defines the internal volume of the reservoir/container.

In certain embodiments of the invention, the reservoir/container is in the form of a pouch having a total internal volume of between 1 l and 1000 l, preferably between 10 l and 200 l, and even more preferably between 10 l and 50 l.

The pouch may comprise at least one base and one cap.

In certain embodiments of the invention, the packaging is in the form of a Bag-in-Box and also comprises a cardboard box comprising an opening. In certain embodiments, the base of the pouch is screwed or clipped into the opening of the carton. In other embodiments, the base of the pouch is not attached to the opening of the carton.

In a fourth aspect, the present invention relates to the use of a plastic material of the invention for the manufacture of a reservoir/container intended to receive a liquid or semi-liquid ingredient which produces gas, preferably $CO_2$.

In a fifth aspect, the present invention relates to the use of a packaging of the invention for the storage and the use of a liquid or semi-liquid ingredient which produces gas, preferably $CO_2$, characterized in that the packaging allows the gas produced to be removed/evacuated.

In a sixth aspect, the present invention relates to a method for storing and using a liquid or semi-liquid ingredient which produces gas, preferably $CO_2$, comprising the following steps:
  packaging the ingredient which produces gas in a packaging of the invention.
  storing, at a temperature of between 0 and 6° C. and in a relative humidity of between 50% and 100%, said packaged ingredient until its use, and
  using the liquid or semi-liquid ingredient which produces gas.

In certain preferred embodiments of the invention, the liquid or semi-liquid ingredient which produces gas comprises a leaven or a yeast, in particular a liquid yeast or a cream yeast.

A more detailed description of certain preferred embodiments of the invention is given below.

DETAILED DESCRIPTION OF THE INVENTION

As mentioned above, the present invention is based on the use of a multilayer plastic film optionally reinforced with a perforated second plastic film, as wrapping/packing for a liquid or semi-liquid ingredient which produces gas, in particular carbon dioxide.

I—Multilayer Plastic Film

A multilayer plastic film according to the invention is characterized by the following properties:
  the film has a B-A-B' type structure,
  the layers making up the film are extruded to a total thickness of between 20 and 50 microns, preferably between 25 and 35 microns, and even more preferably between 27 and 32 microns,
  the permeability of the film to carbon dioxide is greater than or equal to 60 $l/m^2 \cdot 24$ h at delta P=1 bar, and
  the film is slightly impermeable to oxygen ($O_2$) and/or to air and has a permeability to oxygen or less than or equal to 30 $l/m^2 \cdot 24$ h at delta P=1 bar.

The three-layer plastic film according to the invention is generally impermeable to liquid water and preferably to water vapor. Furthermore, since this plastic film is intended to contain the liquid or semi-liquid product containing yeast, it preferably consists of components appropriate according the regulations relating to materials in contact with food products.

In the three-layer B-A-B'-type structure, the compositions of layers B and B' may be identical in all respects. Alternatively, the compositions of layers B and B' may be different.

In certain preferred embodiments, the multilayer plastic film according to the invention has a B-A-B' structure, in which layer A consists of a polymer chosen from polyolefins and olefinic copolymers, and each of layers B and B' comprises a polymer chosen from polyolefins and olefinic copolymers. Polyolefins and olefinic copolymers are hydrophobic and generally have a high chemical inertia, which makes them materials suitable for food wrapping.

The term "polyolefin" or "polyalkene" is intended to mean a synthetic, saturated, aliphatic homopolymer resulting from the polymerization of an olefin. The polyolefins suitable for producing a multilayer film according to the invention include, for example, polyethylene (PE), polypropylene (PP), polymethylene (PMP) which results from the polyaddition of the 4-methylpent-1-ene monomer, and polybutene-1 (PB-1).

The term "olefinic copolymer" is intended to mean a synthetic, saturated, aliphatic copolymer resulting from the polymerization of an olefin, such as ethylene and derivatives thereof, with a monomer other than said olefin. The olefinic copolymers suitable for producing a multilayer film according to the invention include, for example, ethylene-vinyl acetate (EVA) which results from the copolymerization of ethylene and of vinyl acetate; ethylene-polyvinyl alcohol (EVOH) which results from the copolymerization of ethylene and of vinyl alcohol; ethylene-acrylic ester copolymers, such as ethylene-methyl acrylate (EMA) and ethylene-ethyl acrylate (EEA); and ethylene-acrylic ester-maleic anhydride (EAEMA).

In one particular embodiment, layer A consists of an ethylene-vinyl acetate (EVA) with a high vinyl acetate content and each of layers B and B' comprises an ethylene-vinyl acetate (EVA) with a lower vinyl acetate content. The term "EVA with a high vinyl acetate content" is intended to mean herein an EVA containing between 18% and 42% of vinyl acetate, wherein the percentages are percentages by weight. The term "EVA with a lower vinyl acetate content", as used herein, is intended to mean an EVA which contains a lower percentage of vinyl acetate than the EVA which forms layer A. The layers B and B' may be composed of the same ethylene-vinyl acetate (therefore containing the same vinyl acetate content) or of EVA copolymers containing different vinyl acetate contents. In any event, these vinyl acetate contents must be less than that of the EVA which forms layer A. One layer of the B-A-B' structure may have a weight content of vinyl acetate which is constant throughout the entire layer. Alternatively, one layer of the B-A-B' structure may have a composition gradient, wherein the weight content of vinyl acetate is, for example, increased or decreased in a given direction of the layer.

In certain embodiments, layer B or layer B', or else each of layers B and B', comprises, in addition to the polymer, at least one anti-block and/or slip agent. The term "anti-block and/or slip agent", as used herein, is intended to mean any agent which reduces friction, for example between the surface of the final film and the production tool, and/or which has a positive effect on the manipulation of the films by preventing any risk of adhesion. An anti-block and/or slip agent suitable for carrying out the present invention may be chosen from diatomaceous earth, talc, oleamide and erucamide, and combinations thereof. Depending on the nature of the polymer making up layers A, B and B', on the type of machine used for the production of the multilayer film and on its future uses, those skilled in the art will be able to select an anti-block and/or slip agent or a particular combination of such agents, and will be able to determine the required amounts of this or these agent(s) to obtain the desired anti-block and/or slip effect. Layers B and B' may comprise one or more identical anti-block and/or slip agents in the same proportions or different proportions. Alternatively, layers B and B' may comprise one or more different anti-block and/or slip agents, or alternatively one of the layers B and B' may comprise one or more anti-block and/or slip agents and the other layer may not comprise it or them.

The preparation of a multilayer plastic film according to the invention can be carried out using any appropriate method known in the art. In certain preferred embodiments, the three-layer plastic film is prepared by colamination or by coextrusion. The coextrusion may be carried out using a flat die extrusion (termed cast extrusion) technique or an extrusion-blow molding technique. Those skilled in the art will be able to select the most appropriate technique according to the composition of the multilayer plastic film and/or the dimensions of the film to be prepared. Those skilled in the art will also be able to determine the operating temperature, pressure and relative humidity conditions which are optimal for implementing the technique selected.

Surprisingly, the present Applicant has noted that, in order to allow efficient daily evacuation of $CO_2$ while at the same time allowing the production of flexible bags on commonly used shaping machines, the three-layer plastic film must have a thickness of between 20 microns and 50 microns, preferably between 25 microns and 35 microns, and even more preferably between 27 microns and 32 microns.

The utility of the multilayer plastic film according to the invention in the wrapping/packing of liquid or semi-liquid products which produce gas, and in particular of liquid or semi-liquid products containing yeasts, is a result of its gas-permeability properties. More specifically, a film according to the invention has a permeability to $CO_2$ of greater than or equal to 80 $l/m^2 \cdot 24$ h at delta P=1 bar, preferably greater than or equal to 90 $l/m^2 \cdot 24$ h at delta P=1 bar, and is slightly impermeable to oxygen and/or to air. As used herein, the term "impermeable to oxygen and/or to air" is intended to mean a film which has a permeability to oxygen ($O_2$) which is less than or equal to 30 $l/m^2 \cdot 24$ h at delta P=1 bar.

According to the invention, the permeabilities to $CO_2$ and to $O_2$, also called coefficients of permeability (CP), are defined as the coefficients of transmission respectively of carbon dioxide and of oxygen, expressed in $cm^3$ per $m^2$ per 24 h per bar ($cm^3/m^2 \cdot 24$ h·bar or $l/m^2 \cdot 24$ h·bar) and measured according ISO standard 15105-2:2003 annex B using a method with katharometric detection on a gas chromatograph with an injection valve and a sampling loop. Prior to the measurement, the material is conditioned for 48 hours at 23° C. and at a gas moisture content of 0% RH. The measurement of the coefficient of permeability is carried out at a temperature of 23° C., with a gas humidity of 0% RH. The external face of the material is subjected to the test gases and the measurements are carried out on three test specimens of 50 $cm^2$. The test gas consists of a mixture of 50% oxygen and 50% carbon dioxide. The chromatographic detection is carried out using a Porapak® Q detector with a detector temperature of 140° C., and a filament current of 200 mA after calibration of the chromatograph with gas standards having a known oxygen and carbon dioxide concentration.

For greater accuracy in the measurements of coefficients of slight permeability CP to $O_2$, (i.e. less than 5000 $cm^3/m^2 \cdot 24$ h·bar), the measurement is carried out according to ISO standard 15105-2:2003 annex A and ASTM standard D 3985-05 using a Systech 8000 apparatus. Prior to the measurement, the material is conditioned for 48 hours at 23° C. and a gas moisture content of 0% RH. The measurement of the coefficient of permeability is carried out at a temperature of 23° C., with a gas moisture content of 0% RH. The external face of the material is subjected to the test gases and the measurements are carried out with 21% oxygen on three test specimens of 0.5 dm². The stabilization time is 24 hours.

If the detection threshold of the apparatus is reached, it is possible to reduce the $O_2$ content of the test gases and/or the surface area measured so as to thus again be placed under the detection conditions. All that is then required is to weight the result obtained by the reduction of content applied and/or the reduction of surface area applied.

For a measurement of coefficient of $CO_2$ permeability only, it is also possible to apply the method of detection by flame ionization on a gas chromatograph with an injection valve and a sampling loop in accordance with ISO standard 15105-2:2003 annex B.

II—Plastic Material

A plastic material according to the invention is composed of two plastic films, wherein the first is a multilayer plastic film as described above and the second plastic film is perforated and/or has a $CO_2$ permeability greater than or equal to that of the first plastic film. The second plastic film has two roles: it confers mechanical strength to the flexible bag thus produced, and its permeability and/or its perforations allow evacuation of the gas produced by the yeast due to the permeability of the first plastic film.

Surprisingly, the present Applicant has noted that, when the second plastic film does not have a permeability to $CO_2$ greater than or equal to that of the first plastic film, only perforation distributed over the entire surface of the second plastic film allows efficient evacuation of the gas produced by the yeasts. It has also been observed that, in order to allow good evacuation of the gas produced by the yeasts stored in the flexible bags, the perforation density must be high. Thus, the second plastic film must contain at least 1000 perforations/m², preferably at least 5000 perforations/m² and even more preferentially about 7000 perforations/m².

As indicated above, the second plastic film, which is intended to be on the outside of the flexible bag containing the yeasts, confers mechanical strength to this bag. The component(s) of the plastic film will therefore have to be chosen accordingly. The term "mechanical strength", as used herein, is intended to mean any property or combination of properties of hardness, stiffness, flexibility, elasticity, etc., which increases the solidity of the flexible bag. For example, the mechanical strength may be a resistance to being dropped and/or a resistance to impacts. It is, in fact, desirable for the reservoirs containing the liquid or semi-liquid products to remain leaktight during an impact, given that, during the transportation of industrial products, it is virtually inevitable that they will occasionally be dropped.

In certain preferred embodiments, the component(s) of the second plastic film is/are chosen from polyethylene (PE), high-density polyethylene (HDPE), low-density polyethylene (LDPE), linear low-density polyethylene (LLDPE), polycarbonate, polyester, polyethylene terephthalate (PET), polytetrafluoroethylene (PTFE), polypropylene (PP), polyamide (PA) and oriented polyamide (OPA), and mixtures and/or combinations thereof. In particular, the second plastic film may be advantageously composed of oriented polyamide (OPA) and of polyethylene (PE) or of polyethylene terephthalate (PET) and of polyethylene (PE). The second plastic film may, for example, be obtained by extrusion, coextrusion or lamination.

The preparation of the plastic material according to the invention may be carried out by any method known in the art, provided that, in the resulting plastic, each of the two plastic films can perform its role(s) (i.e. in particular, permeability to carbon dioxide and slight permeability to oxygen and/or to air for the first plastic film, mechanical strength and evacuation of the gas by virtue of the perforations or of the permeability to $CO_2$ for the second plastic film). In certain preferred embodiments, the first and second plastic films are assembled only at the time of manufacture of the flexible bag, for example by welding of the two films on the four sides of the bag. Another example is the bag-in-bag system, in which the bags are attached to one another, either on the four sides, or only at the level of the base.

III—Packaging

A packaging according to the invention generally comprises a reservoir or container consisting of a plastic material as described above, in which the first plastic film defines the internal volume of the reservoir in which the liquid or semi-liquid product which produces gas is to be contained. The reservoir or container may be of any shape (cylindrical, cubic, parallelepipedal, flat, etc.) and/or any dimensions. In certain preferred embodiments, the reservoir or container is a flexible bag or a pouch that is relatively flat, in particular a flexible bag or pouch intended to be used in a Bag-in-Box system.

According to certain embodiments, a pouch according to the invention may contain at least 20 g of liquid or semi-liquid product which produces gas, for example between 25 g and 600 g of product for applications intended for consumers of the general public market. In such embodiments, the pouch is a flexible bag having a total internal volume of between 20 ml and 800 ml, preferably between 20 ml and 500 ml.

According to other embodiments, a pouch according to the invention may contain at least 5 kg of liquid or semi-liquid product which produces gas, for example between 10 kg and 1000 kg of product, or between 10 kg and 100 kg of product, or else between 10 kg and 50 kg of product for applications intended for professionals, for example those working in the bakery trade, for instance bakers or industrial bakeries. In such embodiments, the pouch is a flexible bag having a total internal volume of between 1 l and 1000 l, for example between 10 l and 200 l, or between 50 l and 500 l, or else between 500 l and 1000 l.

A pouch according to the invention may contain one or more bases which have a screw thread or rings for screwing on or clipping on a cap. Such bases make it possible to fill and/or empty the pouch (see, for example, U.S. Pat. No. 4,863,770). Generally, at least one base will be located at the bottom, during use, such that the liquid or semi-liquid product can be drawn off by gravity or siphoned. The bag or pouch may also have means for easier and/or more complete emptying or draining of the bag or pouch. Such means are in particular described in DE-A-3 502 455, WO 89/00535, WO 85/0483. WO 90/06888, WO 01/79072 and EP-A-0 138 620.

In certain embodiments, a pouch according to the invention may allow the user to determine or estimate, visually, the amount of liquid or semi-liquid product present in the pouch. In particular, the pouch may be transparent or translucent, or may comprise one or more transparent or translucent parts.

In certain embodiments, a packaging according to the invention is in Bag-in-Box form. In such embodiments, the packaging comprises, in addition to the flexible bag or pouch, a supporting wire basket or a rigid (self-supporting) box which can contain this bag or pouch, as described, for example, in U.S. Pat. No. 6,223,981. The rigid box may be a carton.

IV—Use of the Packaging
Liquid or Semi-Liquid Ingredients which Produce Gas

A packaging according to the present invention may be used for the storage of any liquid or semi-liquid ingredient which produces gas, in particular $CO_2$. In certain embodiments of the invention, the liquid or semi-liquid ingredient which produces gas comprises a yeast or a leaven. In certain particular embodiments of the invention, the ingredient is a liquid yeast or a cream yeast.

The expression "liquid or semi-liquid ingredient containing yeast" is intended to mean a liquid suspension, typically an aqueous suspension, comprising yeast. This generally involves fresh yeast or dry yeast which has been resuspended. According to one preferred embodiment of the present invention, the yeast is a fresh yeast. Advantageously, said yeast, at the time it is packaged, comprises at least $10^5$ colony-forming units (CFU) of yeast per gram, preferably at least $10^8$ colony-forming units (CFU) of yeast per gram, and advantageously at least $10^9$ colony-forming units (CFU) of yeast per gram.

Preferably, the liquid ingredient containing yeast has a content of at least 0.03% by weight of dry matter of live yeast cells, more preferably of at least 0.1%, and even more preferably of at least 5% of dry matter of yeast.

The packaging according to the invention is particularly suitable for storing yeasts used for their fermentative activity. They are in particular yeasts belonging to the family Saccharomycetaceae (classification of The Yeasts, A Taxonomic Study, Kurtzman C. P. and Fell C. W., 4th edition, Elsevier, 1998). The invention thus relates principally to the storage of baker's yeasts, but also relates to the storage of enological, distiller's and/or brewer's yeasts for which problems of storage in liquid or semi-liquid form arise.

The enological, distiller's and/or brewer's yeasts are preferentially chosen from the *Saccharomyces* genus, especially *S. bavanus* and *S. cerevisiae*, in particular the varieties *uvarum*, *calbergensis* and *cerevisiae*, the *Kluyveromyces* genus, in particular *K. thermotolerans*, the *Brettanomyces* genus, especially *B. bruxellensis*, and the *Torulaspora* genus, in particular *T. delbrueckii*, alone or as a mixture.

The baker's yeast is preferentially a yeast chosen from *Saccharomyces cerevisiae*, *Saccharomyces chevalierii* and *Saccharomyces boulardii*.

The ingredient which produces gas (for example the ingredient containing yeast) is liquid or semi-liquid, i.e. it has a viscosity of less than 20,000 centipoises, preferably less than or equal to 1000 centipoises, measured at a temperature of approximately 10° C. using a standard viscometer, for example a J.P. Selecta ST2001 viscometer (L1=needle; speed=10 rpm up to a viscosity of 600 centipoises, speed=1.5 rpm above 600 centipoises) on a sample of 500 ml. Baker's doughs are not typically liquid or semi-liquid products.

The liquid or semi-liquid ingredient containing yeast has a density preferably between 1.01 and 1.25, and even more preferably between 1.05 and 1.15.

The expression "liquid or semi-liquid ingredient containing yeast" denotes, in particular according to the present invention, cream yeast, preferably baker's cream yeast, and liquid leaven.

The expression "cream yeast, preferably baker's cream yeast" is understood to mean a liquid suspension, typically an aqueous suspension, of live yeast cells, preferably baker's yeast cells, said suspension having a preferential dry matter content of at least 12% by weight and generally of between 12% and 50% by weight (broad definition of cream yeast). Preferably, the liquid or semi-liquid cream yeast corresponds to the definition of cream yeast in the strict sense, i.e. it has a dry matter content of between 12% and 25% by weight, and even more preferably between 15% and 22% by weight. However, the present invention is also of use for cream yeasts, preferably baker's cream yeasts, with a higher dry matter content, i.e. of at least 25% by weight, such as, in particular, "high-density" baker's cream yeasts containing one or more osmotic agents, for instance edible polyhydroxy compounds and edible salts. Such high-density baker's cream yeasts, which may in particular have a dry matter content of from 25% to 48% by weight, or else from 25% to 46% by weight, are known and are, for example, described in WO 91/12315 and WO 03/048342.

The term "liquid leaven" is understood to mean, according to the invention, a liquid suspension, typically an aqueous suspension, of live yeast cells, preferably baker's yeast cells, of live lactic acid bacteria cells and of flour. Preferably, the liquid leaven has a dry matter content of between 12% and 20% by weight, and more preferentially of between 15% and 17% by weight.

Stable, ready-to-use liquid bread leavens suitable for being packaged according to the invention are in particular those described, by the applicant, in European patent number EP 0 953 288-B1 and international application WO 2004/080187.

Advantageously, the liquid leaven is obtained by using a culture medium comprising at least one unmalted cereal flour and water, by carrying out an inoculation with at least one preparation of heterofermentative lactic acid bacteria and at least one preparation of yeast, preferably by additionally using at least one malted cereal flour providing amylases or any equivalent source of amylases and/or carrying out at least one inoculation with a preparation of homofermentative lactic acid bacteria. At the time it is packaged, it thus preferably comprises at least $10^6$ colony-forming units (CFU) of lactic acid bacteria per gram and at least $10^4$ colony-forming units (CFU) of yeast per gram and even more preferentially at least $10^9$ colony-forming units (CFU) of lactic acid bacteria per gram and at least $10^6$ colony-forming units (CFU) of yeast per gram, has a stable final pH of between 4 and 4.3 and a dry matter content of between 13% and 20% and preferentially contains from 15 to 30 g/kg of lactic acid and from 6 to 10 g/kg of acetic acid. The preparation of such a leaven is described, for example, in European patent number EP 0 953 288-B1.

Another particularly advantageous ready-to-use liquid bread leaven according to the present invention comprises a flour-based culture medium containing at least one cereal flour and water, said medium being inoculated and fermented with at least homofermentative lactic acid bacteria which bioconvert lactic acid and being inoculated with at least one preparation of yeasts, preferentially baker's yeasts. The ready-to-use liquid bread leaven preferentially also comprises at least one malted cereal flour providing amylases or any equivalent source of amylases. It thus comprises $10^8$ colony-forming units (CFU) of lactic acid bacteria, of which 60% are homofermentative lactic acid bacteria which bioconvert lactic acid, per gram, and at least $10^6$ colony-forming units (CFU) of yeast per gram, has a stable final pH of between 3.8 and 4.5 and a dry matter content of between 27% and 35%, and contains at least 7 g of acetic acid, preferentially from 15 to 20 g/kg of lactic acid and from 7 to 10 g/kg of acetic acid.

Preferably, the yeasts used for the leaven preparation may be *Saccharomyces chevalierii* yeasts, the homofermentative bacteria are those of the *Lactobacillus plantarum* and/or *casei* species, and the heterofermentative strains are those of the *Lactobacillus brevis* species.

In certain embodiments, the liquid yeast product, preferably liquid fresh yeast product, in particular the liquid cream yeast and the liquid leaven, are stabilized by adding one or more food stabilizers. These stabilizers delay or prevent the settling out of the yeast cells in the suspension. By virtue of their presence in the suspension, the liquid fresh yeast product, preferably the cream yeast or the liquid leaven, retains its homogeneity for longer when it is stored without agitation. Among the various food stabilizers that are of use for stabilizing cream yeast, mention may be made of gums, such as xanthan gum, and thermally and/or chemically modified starches, such as acetylated distarch adipate corresponding to the definition of the modified starch E1422. Such stabilized cream yeasts are, for example, described in EP-A-0 792 930.

The yeast or leaven compositions may also contain additives or aids, the role of which is to act as a bread-making improver and/or to maintain the homogeneity of the suspension. These additives may be oxidizing agents such as ascorbic acid, reducing agents such as L-cysteine, enzymatic preparations which have one or more enzymatic activities, for instance amylase, xylanase, lipase and/or phospholipidase preparations, or oxidase, for instance glucose oxidase. These additives may also be one or more osmotic acids, for instance edible polyhydroxy compounds and edible salts.

Storage of Liquid or Semi-liquid Ingredients which Produce Gas

A subject of the present invention is also the use of a packaging as described above for storing a liquid or semi-liquid ingredient which produces gas, in particular a liquid or semi-liquid ingredient containing yeast as described above. Such packaging is more particularly used at temperatures below 8° C. preferably between 0° C. and 6° C., and a relative humidity of between 50% and 100%, and allows good storage of the liquid or semi-liquid products containing yeasts for at least 4 weeks, preferably for at least 6 weeks, and even more preferably for at least 8 weeks.

Under these storage conditions, such a packaging may, in addition, be used with a potential variation in temperature which can range up to 35° C. for a maximum period of 8 hours, and preferably for 4 hours, and even more preferably which can range up to 20° C. for a maximum period of 2 hours.

Unless otherwise defined, all the technical and scientific terms used in the description have the same meaning as that commonly understood by an ordinary specialist in the field to which this invention belongs. Likewise, all the publications, all the patent applications, all the patents and any other references mentioned herein are incorporated by way of reference.

EXAMPLES

The following examples describe some embodiments of the present invention. However, it is understood that the examples are presented merely by way of illustration and in no way limit the scope of the invention.

Example 1

Three-layer films based on ethylene vinyl acetate (EVA) were prepared using blown film extrusion techniques well known to those skilled in the art. Two films, film 1 and film 2, were obtained with a thickness of 30 μm and 40 μm, respectively. The central layer A of each of these films consisted of an EVA having a weight content of vinyl acetate of between 18% and 42%, and the external layers B and B' were made of EVA having a weight content of vinyl acetate which is less than that of the EVA of the layer A.

Permeability Measurements. The oxygen and carbon dioxide transmission coefficients were determined on a sample of film under standard conditions and after conditioning in a climatic chamber at 23° C. and 90% relative humidity (RH) for 48 hours.

The oxygen and carbon dioxide transmission coefficients were determined using an LYSSY GPM5000 apparatus. Each sample was placed in a test cell of 50 cm$^2$ between two chambers, the lower chamber being constantly flushed with a stream of helium and the other chamber being in contact with the test gas (a $CO_2/O_2/N_2$ mixture in the proportions 1/3, 1/3, 1/3). Any gas which passes through the film sample is transported by the vector gas to the gas chromatograph equipped with a katharometer detector. The experimental conditions used were the following:

vector gas: helium,
test gas: mixture in the proportions 1/3, 1/3, 1/3 of $CO_2/O_2/N_2$,
test temperature: 23° C.,
the films are tested as such and then after conditioning at 23° C. and 90% RH for 48 hours.

The thickness of the film sample was measured using an Adamel Lhomargie precision micrometer (precision 1 μm). The measurements were carried out on three different samples of each film.

Results. The results obtained are presented in the following Tables 1 and 2, in which $PCO_2$ and $PO_2$ are expressed in l/m$^2$/24 h/atm.

TABLE 1

Thickness and oxygen and carbon dioxide transmission coefficients for three samples of film 1

| Film 1 | | Thickness (μm) | $PCO_2$ | $PO_2$ |
|---|---|---|---|---|
| Standard conditions | Sample 1 | 28 | 87 | 14 |
| | Sample 2 | 77 | 87 | 21 |
| | Sample 3 | 26 | 93 | 18 |
| After conditioning | Sample 1 | 25 | 101 | 19 |
| | Sample 2 | 28 | 111 | 73 |
| | Sample 3 | 20 | 121 | 26 |

TABLE 2

Thickness and oxygen and carbon dioxide transmission coefficients for three samples of film 2

| Film 2 | | Thickness (μm) | $PCO_2$ | $PO_2$ |
|---|---|---|---|---|
| Standard conditions | Sample 1 | 36 | 66 | 12 |
| | Sample 2 | 37 | 80 | 15 |
| | Sample 3 | 34 | 87 | 16 |
| After conditioning | Sample 1 | 39 | 78 | 14 |
| | Sample 2 | 37 | 91 | 18 |
| | Sample 3 | 39 | 88 | 19 |

The permeabilities of the films before and after conditioning do not significantly differ.

Example 2

Pouches of 10 and 20 kg, intended for the wrapping/packing of liquid yeast and/or of cream yeast, were prepared using the films of Example 1. The empty pouches have a rectangular or square shape with internal dimensions of 500×680 for the 20 kg pouches and 500×500 for the 10 kg pouches.

The pouches were reinforced with a second multilayer film having the following composition: a layer of 20 μm of OPA (Nylon) having a density of 23 g/m$^2$, a layer of adhesive, and a layer of 80 µm of LLDPE/LDPE having a density of 74 g/m$^2$.

The second film is perforated, comprising 7090 perforations per m$^2$. The pouches were equipped with a screw-in base positioned 105 mm from the upper sealing.

Control pouches were used as controls. These control pouches consisted of a film of polyethylene slightly permeable to $CO_2$ (permeability of 17 to 27 l/m$^2$/24 h at delta P=1 bar), and had a degasser cap which allowed the evacuation of the carbon dioxide produced during storage and transportation.

Test for measuring gas given off. The objective of this test was to evaluate the amount of $CO_2$ which is leaked, during storage, through a Bag-in-Box (BIB) according to the invention (i.e. "carton+pouch according to the invention") and through a control BIB (i.e. "carton+control pouch") after each has been filled with a liquid product containing yeast resulting from the same production. To this end, each filled BIB was placed entirely in a leaktight bag. Thus, any gas which is leaked from the wrapping system is trapped in the bag. Each day, this gas was emptied from the leaktight bag while being measured using the principle of the measuring cylinder: the system, similar to a measuring cylinder, is first of all filled with water. The tap of the pouch containing the BIB and of the measuring cylinder are then opened. The gas drives off the water and the volume of gas thus evacuated is measured. The results obtained are reported in the following Table 3.

TABLE 3

Amount of $CO_2$ which is leaked from the various BIBs tested as a function of storage time

| Storage time (days) | BIB 10 kg | | BIB 20 kg | |
| --- | --- | --- | --- | --- |
| | according to the invention (ml) | control (ml) | according to the invention (ml) | control (ml) |
| 1 | 1860 | 1220 | 2220 | 2100 |
| 2 | | | | |
| 3 | 2320 | 2480 | 4320 | 4400 |
| 4 | | | | |
| 5 | | | | |
| 6 | 3500 | 3680 | 7120 | 7200 |
| 7 | 1100 | 1040 | 2300 | 2300 |
| 8 | 1080 | 1140 | 1280 | 1260 |
| 9 | 360 | 800 | 1460 | 1320 |
| 10 | 1080 | 1180 | 2300 | 2200 |
| 11 | | | | |
| 12 | | | | |
| 13 | 7580 | 2840 | 4940 | 5340 |
| 14 | 890 | 1600 | 1120 | 1290 |
| 15 | 900 | 1140 | 1300 | 1440 |
| 16 | | | | |
| 17 | 1980 | 1960 | 3560 | 4200 |
| 18 | | | | |
| 19 | | | | |
| 20 | 3060 | 3180 | 5200 | 5400 |
| 21 | 980 | 920 | 1260 | 1320 |
| 22 | 1200 | 1200 | 2080 | 2180 |
| 23 | 1000 | 980 | 1260 | 1500 |
| 24 | 1080 | 980 | 2080 | 1560 |
| Total (ml) | 24970 | 26340 | 43800 | 45010 |
| Average per day (liter) | 1.04 | 1.10 | 1.83 | 1.88 |

As can be noted in Table 3, the behavior of the BIBs according to the invention and the behavior of the control BIBs are identical, both in terms of average amount of gas leaked per day, and of the total volume of $CO_2$ leaked during the 24 days of the tests (as shown in Table 4).

TABLE 4

Total amount of $CO_2$ leaked from the various BIBs in 24 days of storage

| | BIB 10 kg | | BIB 20 kg | |
| --- | --- | --- | --- | --- |
| | according to the invention (ml) | control (ml) | according to the invention (ml) | control (ml) |
| Total volume of $CO_2$ leaked in 24 hours (liter) | 25 | 27 | 44 | 45 |

The invention claimed is:

1. Method for the storage of a liquid or semi-liquid yeast or leaven, said method comprising a step of:
    storing the liquid or semi-liquid yeast or leaven in a packaging,
    wherein:
    the packaging comprises a container composed of two plastic films, wherein the first plastic film is a three-layer plastic film with a B-A-B' structure and the second plastic film is uniformly perforated;
    the first plastic film defines the internal volume of the container; and
    the container is in the form of a pouch having a total internal volume of between 1 liter and 1000 liters;
    and wherein:
    layer A of the three-layer plastic film consists of an ethylene-vinyl acetate (EVA) with a high vinyl acetate content, as percentage by weight, of between 18% and 42%, and
    each of layers B and B' of the three-layer plastic film consists of an ethylene-vinyl acetate (EVA) having a vinyl acetate content, as percentage by weight, which is lower than that of the ethylene-vinyl acetate of layer A,
    the permeability of the three-layer plastic film to carbon dioxide, measured according to ISO standard 15105-2:2003 annex B, is greater than or equal to 80 l/m$^2$·24 h at delta P=1 bar,
    the three-layer plastic film has a total thickness of from 20 to 50 microns, and
    the permeability of the three-layer plastic film to oxygen ($O_2$), measured according to ISO standard 1510-2:2003 annex B, is less than or equal to 30 l/m$^2$·24 h at delta P=1 bar.

2. The method according to claim 1, wherein the liquid or semi-liquid yeast is a cream yeast.

3. The method according to claim 1, wherein the permeability of the three-layer plastic film to carbon dioxide, measured according to ISO standard 15105-2:2003 annex B, is greater than or equal to 90 l/m$^2$·24 h at delta P=1 bar.

4. The method according to claim 1, wherein the layers B and B' of the three-layer plastic film are identical.

5. The method according to claim 1, wherein the layers B and B' of the three-layer plastic film are different.

6. The method according to claim 1, wherein the container is in the form of a pouch having a total internal volume of between 10 liters and 200 liters.

7. The method according to claim 1, wherein the container is in the form of a pouch having a total internal volume of between 1 liter and 50 liters.

8. The method according to claim 1, wherein the second plastic film is composed of oriented polyamide (OPA) and polyethylene (PE) or of polyethylene terephthalate (PET) and polyethylene (PE).

9. The method according to claim 1, wherein the pouch comprises a base and a cap.

10. The method according to claim 1, wherein the packaging is in the form of a bag-in-box and also comprises a cardboard box comprising an opening.

11. The method according to claim 1 further comprising a step of:
   storing, at a temperature of between 0 and 6° C. and in a relative humidity of between 50% and 100%, said packaged ingredient until use.

12. The method according to claim 2, wherein the cream yeast is a baker's cream yeast.

* * * * *